(12) United States Patent
Yu

(10) Patent No.: US 12,097,042 B2
(45) Date of Patent: Sep. 24, 2024

(54) METHOD FOR DETECTING CARPAL TUNNEL USING AN ULTRASONIC DETECTION DEVICE

(71) Applicant: Hsueh-Chih Yu, Taichung (TW)

(72) Inventor: Hsueh-Chih Yu, Taichung (TW)

( * ) Notice: Subject to any disclaimer, the term of this patent is extended or adjusted under 35 U.S.C. 154(b) by 36 days.

(21) Appl. No.: 17/697,580

(22) Filed: Mar. 17, 2022

(65) Prior Publication Data
US 2023/0293092 A1    Sep. 21, 2023

(51) Int. Cl.
*A61B 5/00*    (2006.01)

(52) U.S. Cl.
CPC .......... *A61B 5/4523* (2013.01); *A61B 5/4533* (2013.01); *A61H 2205/065* (2013.01)

(58) Field of Classification Search
CPC ..... A61B 5/4523; A61B 5/4533; A61B 5/459; A61H 2205/065; G09B 23/00; G09B 23/286
See application file for complete search history.

(56) References Cited

U.S. PATENT DOCUMENTS

| | | | | |
|---|---|---|---|---|
| 5,533,526 A | * | 7/1996 | Goldberg | ....... A61B 17/320036 128/878 |
| 7,135,017 B2 | * | 11/2006 | Klotz | ....................... A61N 7/02 600/471 |
| 2008/0009736 A1 | * | 1/2008 | Amadio | ................ A61B 5/4523 600/453 |
| 2010/0179450 A1 | * | 7/2010 | Abdullah | ............. A61B 5/4523 600/587 |
| 2013/0165962 A1 | * | 6/2013 | Porshinsky | ...... A61B 17/32053 606/185 |
| 2014/0011173 A1 | * | 1/2014 | Tepper | ..................... A61B 8/58 434/273 |

* cited by examiner

*Primary Examiner* — Ashley K Buran
*Assistant Examiner* — Helene Bor
(74) *Attorney, Agent, or Firm* — Chun-Ming Shih; HDLS IPR SERVICES

(57) ABSTRACT

In a method for detecting carpal tunnel using an ultrasonic detection device, the palm is placed on a flat surface, and the fingers are naturally stretched out to form a "5" shape; a mark is placed 0.5 cm above the crease of the palm (Distal wrist crease), and the probe unit of an ultrasonic detection device is placed at the short axis position of the wrist joint. By rotating the probe unit, the probe unit, the marker, and the index finger are on the same axis (index finger axis), so that the image of the carpal tunnel section of the palm can be obtained on a display of the ultrasonic detection device. Accordingly, the detection method is accurate and efficient, correctly guides students and doctors to find the position of the carpal tunnel correctly, and avoids the purposeless search for the position of the carpal tunnel by the probe on the palm, and subsequent treatment.

2 Claims, 14 Drawing Sheets

METHOD FOR DETECTING CARPAL TUNNEL USING AN ULTRASONIC DETECTION DEVICE

TECHNICAL FIELD

The method for detecting carpal tunnel using an ultrasonic detection device, and provides a detecting method that students or doctors can quickly detect the carpal tunnel and perform subsequent processing.

BACKGROUND

Whether in nursing or in medicine, injecting drugs is an indispensable knowledge, and sometimes the injection must be assisted by an instrument to successfully display the injection location, and then prescribe the right medicine to the lesion.

In the treatment or teaching of carpal tunnel syndrome, the teaching manual instructs the students to use the injection needle to inject at the position of the carpal tunnel; as shown in FIG. 1, the position of the carpal tunnel A happens to have multiple nerves B, wrist ligaments C, Tendon D, carpal bone E, and artery F converge. If you are not careful, nerve B or tendon D will be stabbed, causing pain to the patient. Carpal bone E will hinder the injection. Therefore, carpal tunnel A is not searched with the help of instruments. Giving injections is quite difficult and quite dangerous.

As shown in FIG. 2, if the injection is taken from the side of the ulnar artery, it is easy to let the injection needle stick to the ulnar artery, which may cause the risk of finger ischemia (fingers ischemia); as shown in FIG. 3, if the needle is inserted from the radial side, in order to avoid the obstruction of the scaphoid tubercle, the needle must be inserted from the wrist joint, and the radial artery must be avoided first and the needle must be inserted above it; then the radial artery must be avoided. Continuing needle insertion below the distal FCR tendon is difficult to reach the carpal tunnel.

Therefore, how to solve the problems and drawbacks of the prior art have become topics of great concerns of the related suppliers.

SUMMARY OF THE INVENTION

The main objective of the present invention is to provide a method for detecting carpal tunnel using an ultrasonic detection device. The probe of the ultrasonic detection device is used to match the posture of a palm, so that the probe can accurately detect the tunnel joint Location.

Therefore, the method for detecting carpal tunnel using an ultrasonic detection device. Through the technology of the present invention, the position and image of the carpal tunnel can be accurately displayed, so as to assist doctors in the treatment of carpal tunnel syndrome, and avoid injection contacting blood vessels and nerves or tendons for safety purposes.

The method for detecting carpal tunnel using an ultrasonic detection device, comprising of:

Step 1: Lay the palm on a flat surface, with the palm facing up, and naturally straighten and open the fingers to form a "5" shape;

Step 2: Set a mark 0.5 cm above the crease at the bottom of the palm;

Step 3: Match with a super One of the probe units of the sonic detection device is arranged on the short axis (0-180 degree axial direction) of the wrist joint of the test subject, and then the probe unit is slightly rotated near the thumb side, so that the probe unit is rotated to the direction of the index finger, And the axial direction of the probe unit is just on the same axis as the index finger and the mark;

Step 4: Cooperate with the ultrasonic detection device, and the image of the carpal tunnel section of the palm can be obtained by the probe unit on the ultrasonic detection device. a display.

In one embodiment of method for detecting carpal tunnel using an ultrasonic detection device, wherein, in step 2, the position of the crease is just at the great mound.

In one embodiment of method for detecting carpal tunnel using an ultrasonic detection device, wherein, when searching for the right wrist tunnel image, the middle finger of the right hand is 90 degrees, the probe unit is rotated to the right, and the middle finger of the right hand is aligned with the probe unit. The included angle is −20~−25 degrees, in other words, the probe unit is located at a position of about 70 degrees.

In one embodiment of method for detecting carpal tunnel using an ultrasonic detection device, wherein, in step 3, when looking for the left wrist tunnel image, the left middle finger is 90 degrees, the probe unit is rotated to the left, and the left middle finger is 90 degrees. The included angle with the probe unit is 20-25 degrees, in other words, the probe unit is located at a position of about 110 degrees.

In one embodiment of method for detecting carpal tunnel using an ultrasonic detection device, in step 3, the short axis is kept parallel to the image of the display.

Based on the above description, the detection method of the present invention has the following advantages:

1. Compared with the method without the detection instrument, the position of the carpal tunnel can be displayed correctly.
2. The detection method of the present invention is accurate and efficient, correctly guides students and doctors to find the position of the carpal tunnel correctly, and avoids the purposeless search of the position of the carpal tunnel by the probe on the palm.
3. Further, the detection method of the present invention can cooperate with the carpal tunnel treatment method, and inject steroids and other drugs into the carpal tunnel to remove the lesions.
4. Through the technology of the present invention, medical students can quickly find the location of the carpal tunnel and further perform simulated injection, which can provide students with clinical experience in the future.
5. Through the technology of the present invention, in addition to providing a rehabilitative doctor as a diagnosis basis, further traditional Chinese medicine can also cooperate with the technology of the present invention to avoid acupuncture needles from hurting parts other than the carpal tunnel in acupuncture treatment.
6. In addition, during the detection process, a thick towel can be laid under the user's wrist, so that the wrist joint can be fully stretched.

DETAILED DESCRIPTION

Figure 1:
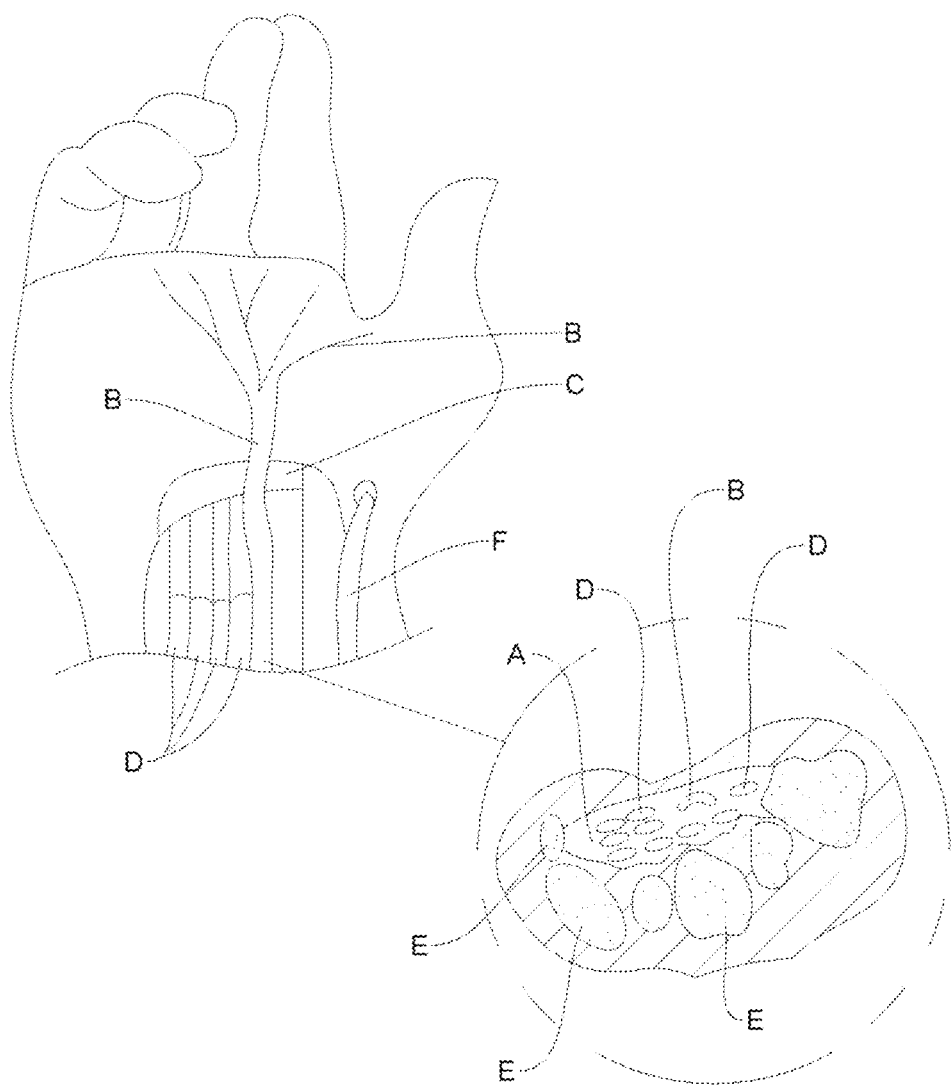
FIG. 1 is a conventional structural diagram of the carpal tunnel.
Figure 2:
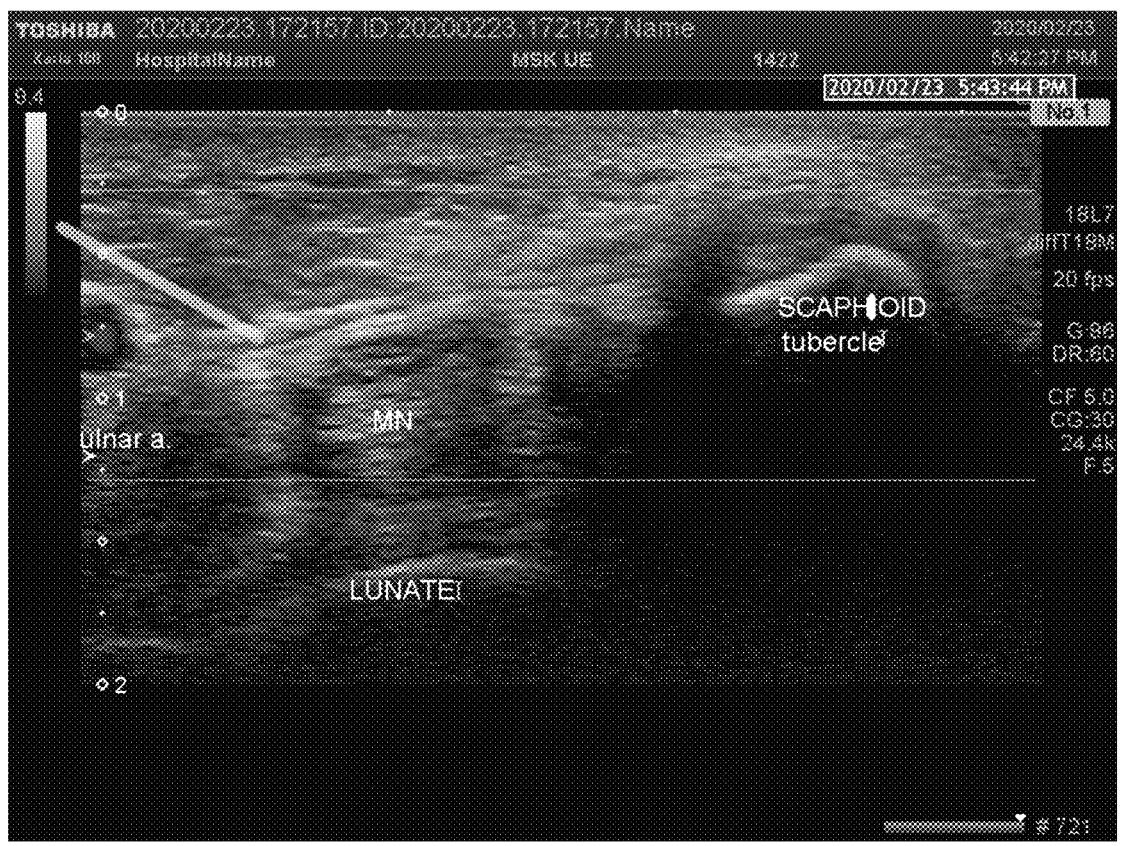
FIG. 2 is a conventional schematic diagram of ultrasound for needle insertion into the ulnar artery.
Figure 3:
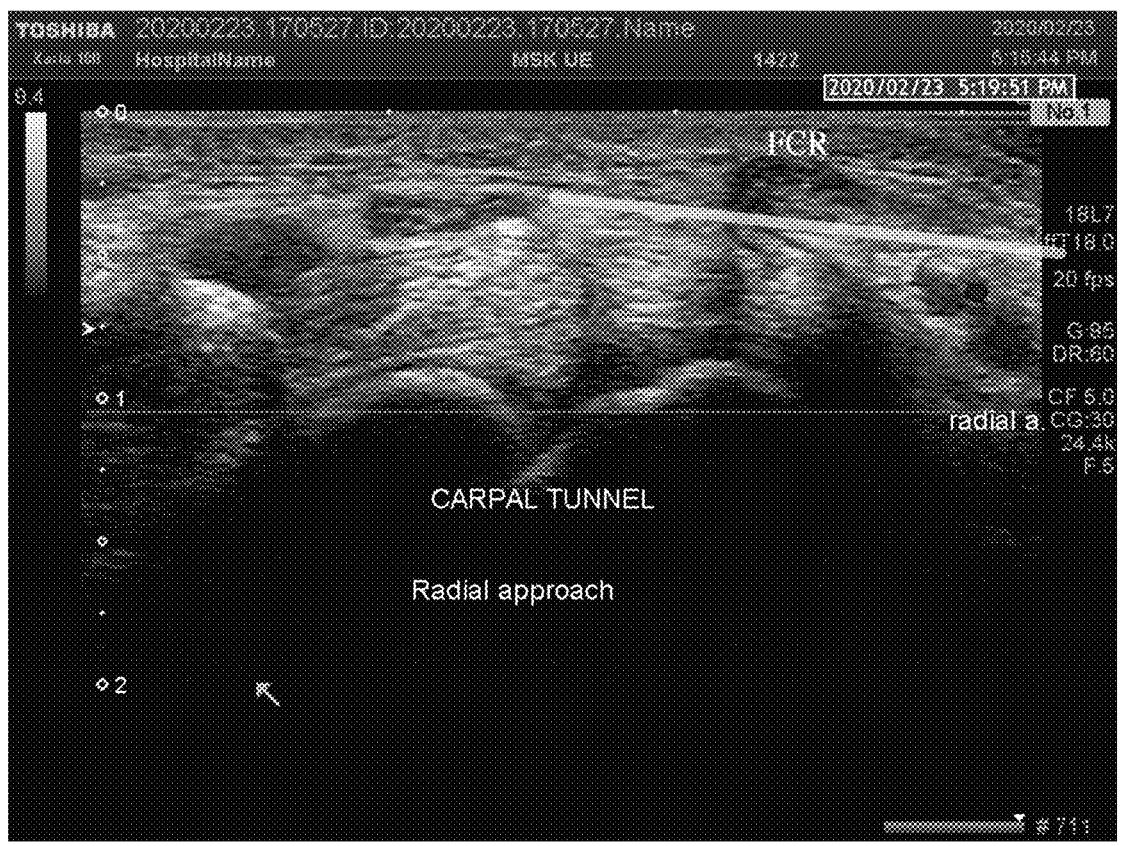
FIG. 3 is a conventional ultrasound schematic diagram of needle insertion from the radial side.
Figure 4:
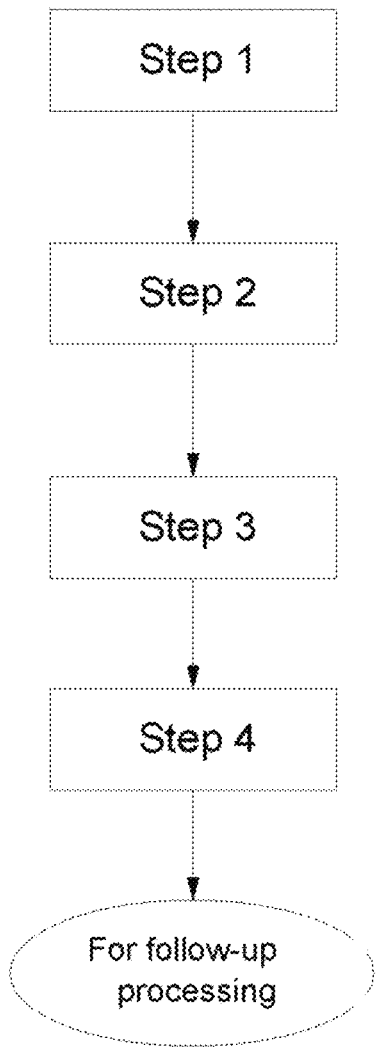
FIG. 4 is a step diagram of the present invention.
Figure 5:
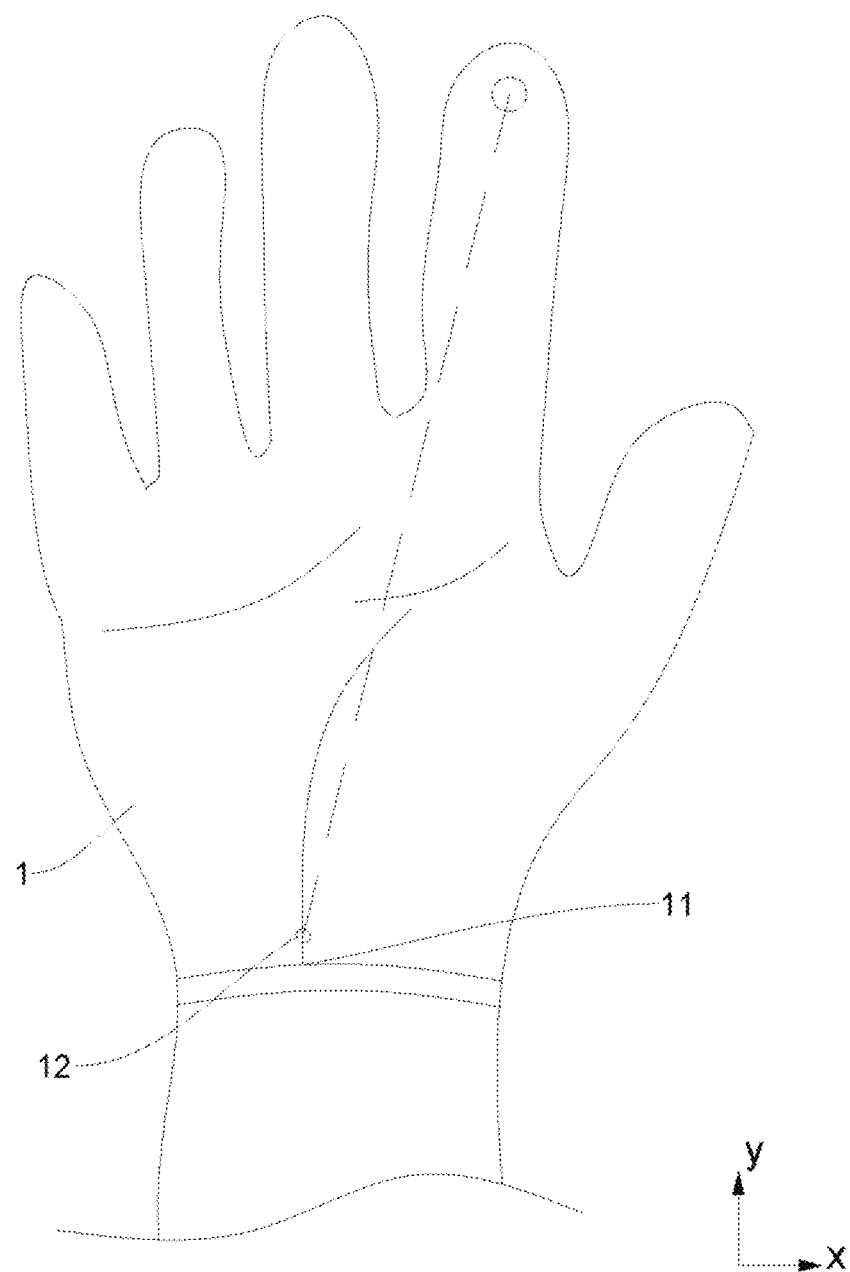
FIG. 5 is a schematic diagram (1) of the detection of the present invention.

In order to let your esteemed reviewer be able to have further understanding and recognition on the features of the present invention, the following better embodiments are presented accompanied with drawings for descriptions:

Please refer to FIG. 4 to FIG. 7, the present invention is a method for detecting carpal tunnel using an ultrasonic detection device. The steps include:

Step 1: As shown in FIG. 4 and FIG. 5, place the palm 1 A on a flat surface, with the palm facing up, and the fingers are naturally straightened and opened to form a "5" shape. For better comfort and to allow the user's wrist to stretch, a thick towel can be placed under the wrist.

Figure 6:
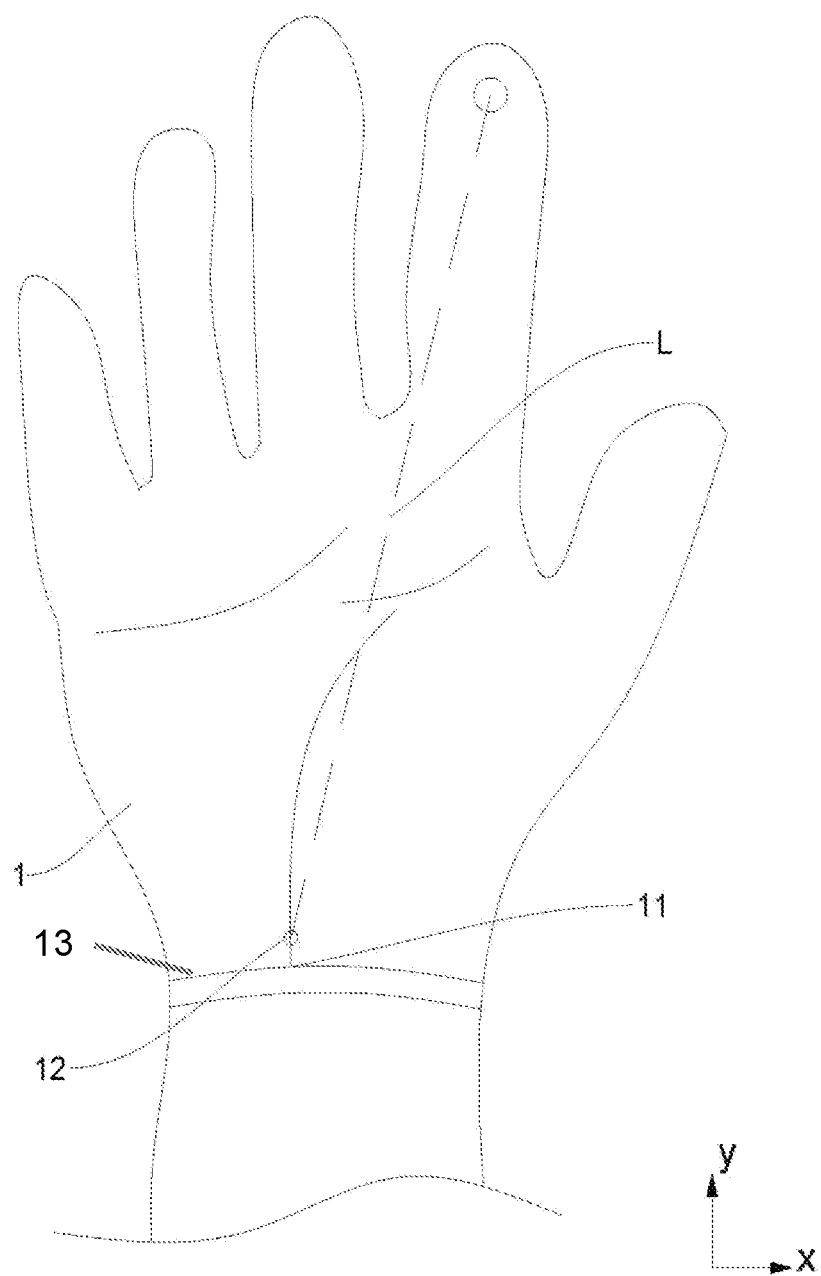
FIG. 6 is a schematic diagram (2) of the detection of the present invention.
Figure 10:
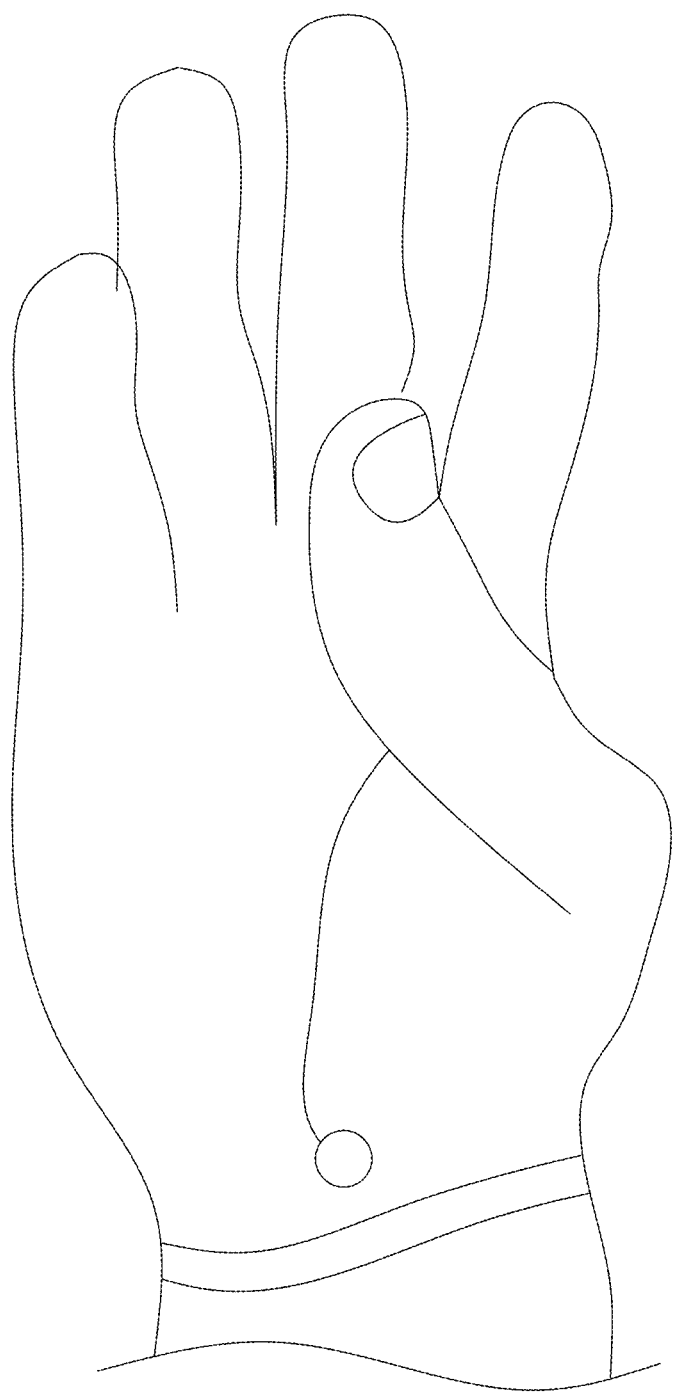
FIG. 10 is the actual marking location.

Step 2: As shown in FIG. 4, FIG. 6, and FIG. 10, set a mark 12 that is, at the top of the Distal wrist crease 13 that is, at the bottom of the lifeline of the palm 0.5 cm above FIG. 10 for the location of the blue dot. If the crease 13 is not clear, the thumb can be moved slightly towards the palm side to produce obvious crease marks; and in terms of acupuncture points in traditional Chinese medicine, the position of the crease 13 just falls on the great mound 11.

Figure 7:
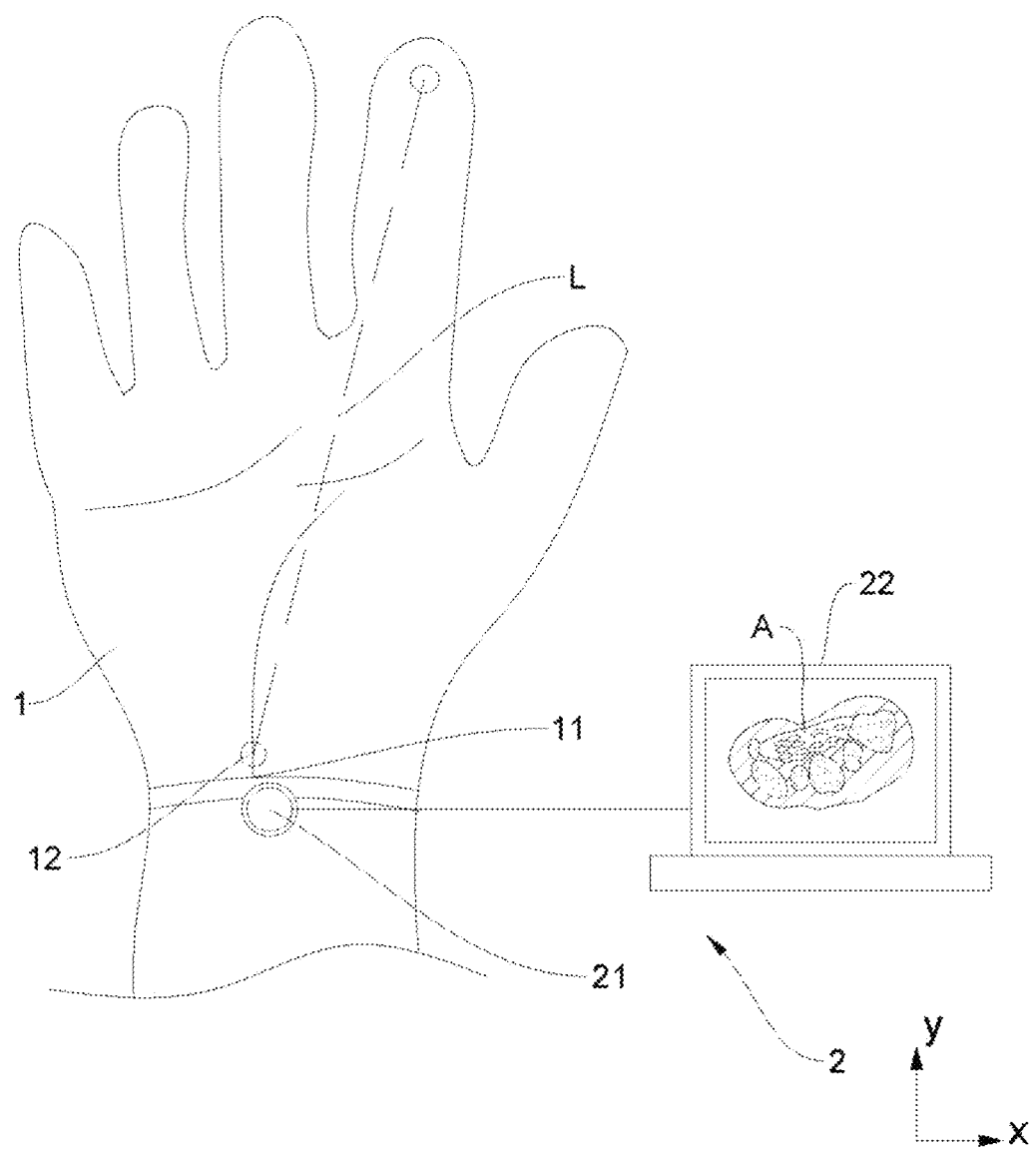
FIG. 7 is a schematic diagram (3) of the detection of the present invention.
Figure 11:
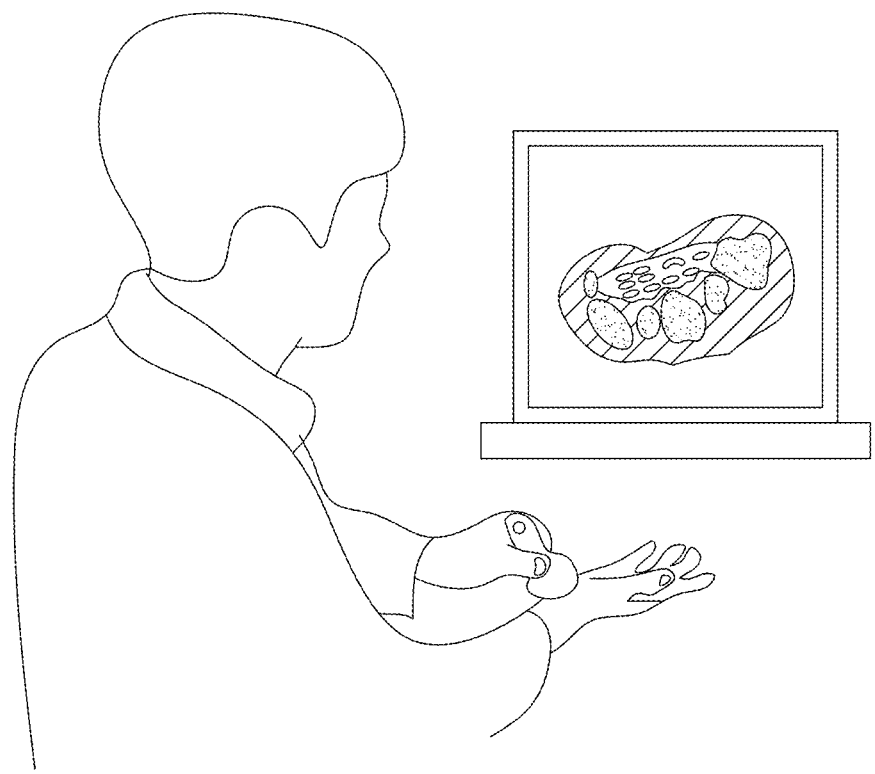
FIG. 11 is a schematic diagram of the detection of the present invention.

Step 3: As shown in FIG. 4, FIG. 7, and FIG. 11, cooperate with a probe unit 21 of an ultrasonic detection device 2 and set it on the short axis (0-180 degree axial direction of the wrist joint of the subject to be tested, the position is in the FIG. 11), then slightly rotate the probe unit 21 near the thumb side, so that the probe unit 21 rotates to the direction of the index finger, and the axial direction of the probe unit 21 is just on the same axis L as the index finger, marked on the same axis L.

In the previous steps, if you want to quantify the angle of rotation, the description is as follows: when looking for the right wrist tunnel image, the middle finger of the right hand is 90 degrees, the probe unit 21 is rotated to the right, and the angle between the right middle finger and the probe unit 21 is −20~−25 degrees, in other words, the probe unit 21 is located at about 70 degrees; on the contrary, when looking for the left wrist tunnel image, the left middle finger is 90 degrees, the probe unit 21 is rotated to the left, and the left middle finger is 90 degrees. The included angle with the probe unit 21 is 20-25 degrees, in other words, the probe unit 21 is located at a position of about 110 degrees.

Figure 12:
FIG. 12 is a schematic diagram of ultrasound used in the short-axis exploration of the carpal tunnel according to the present invention.
Figure 13:
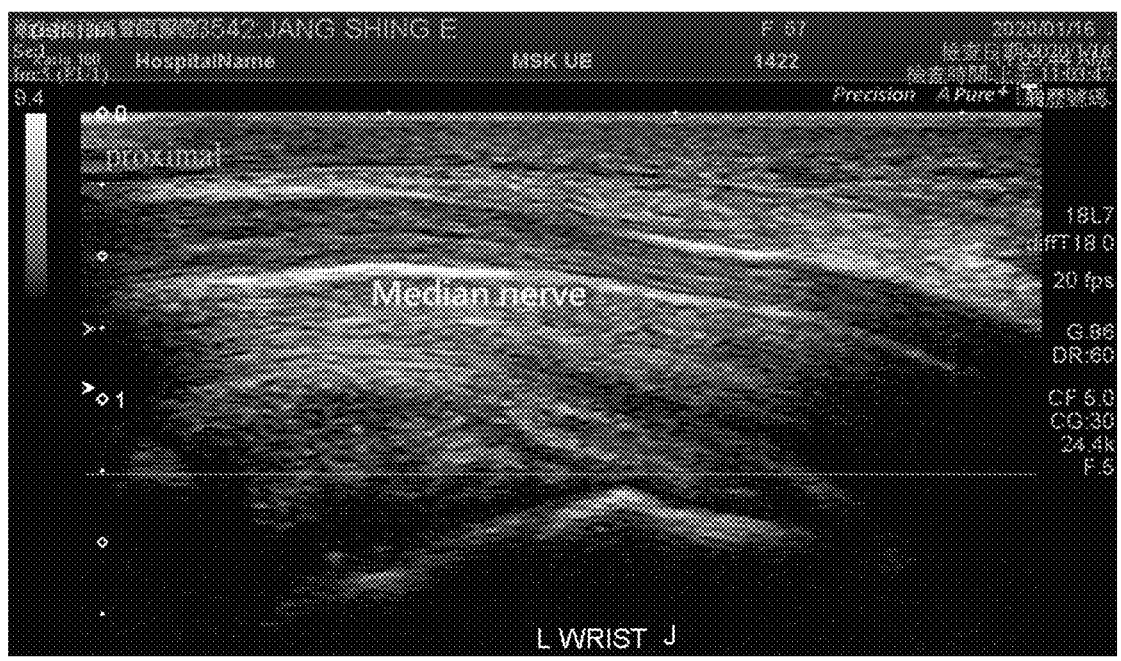
FIG. 13 is a schematic diagram of the ultrasonic wave used in the long-axis exploration of the carpal tunnel according to the present invention.
Figure 14:
FIG. 14 is a schematic diagram of ultrasound used in carpal tunnel treatment according to the present invention.

Step 4: As shown in FIG. 4 and FIG. 7, in conjunction with the ultrasonic detection device 2, the probe unit 21 can obtain an image of the carpal tunnel A section of the palm 1 on a display 22 of the ultrasonic detection device 2. Wherein, in step 3, the short axis is kept parallel to the image of the display 22. FIG. 12 is an ultrasonic schematic diagram of the short-axis exploration of the carpal tunnel by the detection method of the present invention; FIG. 13 is an ultrasonic schematic diagram of the detection method of the present invention in the long-axis exploration of the carpal tunnel; and FIG. 14 is this Invented a schematic diagram of ultrasound used in carpal tunnel treatment.

As shown in FIG. 4 to FIG. 7, through the above steps, the position of the carpal tunnel A can be quickly found. For medical students, there is no need to hold the probe 21 on the wrist aimlessly to find the position of the carpal tunnel A position, and can specifically understand the shape and position of the carpal tunnel A, and then determine the appropriate treatment method through the state displayed on the display 22.

Figure 8:
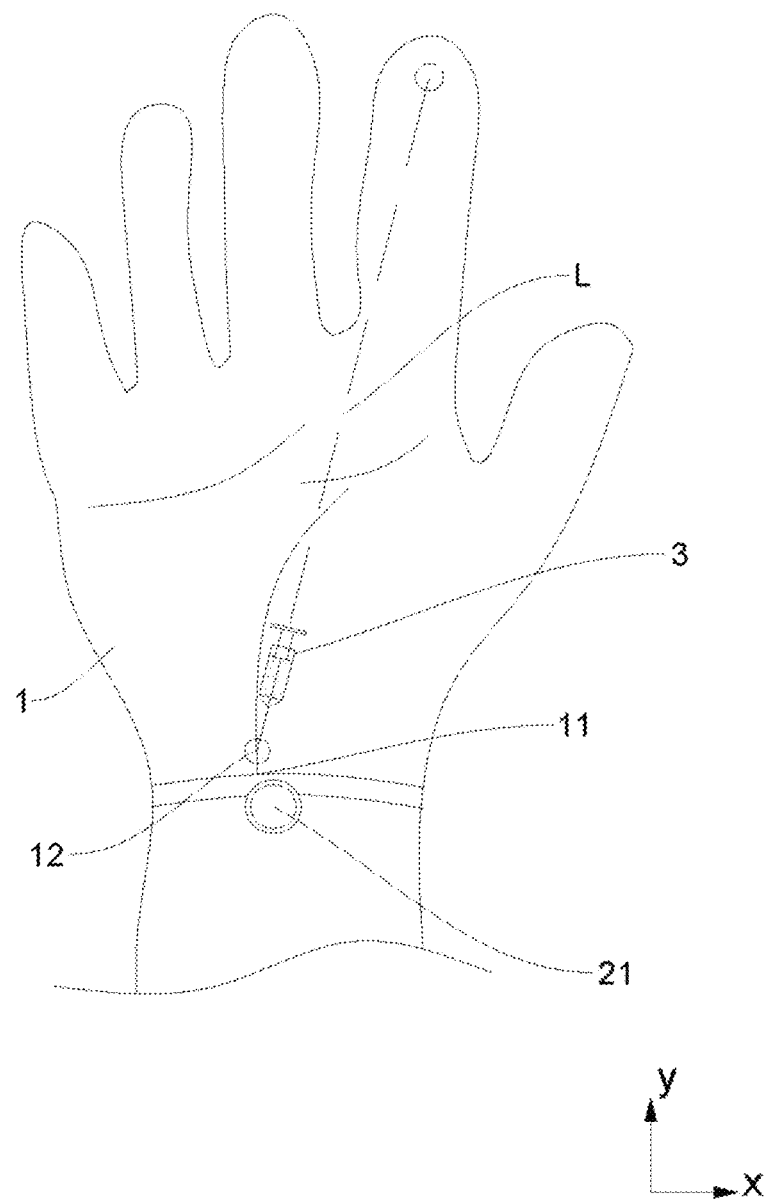
FIG. 8 is a schematic diagram of injection using the detection method of the present invention.

As shown in FIG. 8, for a physician who has already practiced, using the technology developed in the present invention, if the physician needs to judge that a drug needs to be applied to the carpal tunnel A, the three detection steps of the present invention can be used to detect the presence of the carpal tunnel A. Depending on the position and the cut plane, the physician naturally injects the drug into the carpal tunnel A from the opposite side of the probe unit 21 (that is, the inner edge of the scaphoid tubercle) through the syringe 3, and supports the carpal tunnel A through the drug to relieve pain.

Further from the technology of FIG. 8, because the detection technology of the present invention can facilitate the physician to perform needle injection, and avoid the situation that the ulnar needle may pierce the radial artery and nerve, and it is not as difficult as the radial needle, And the simple action can solve the lack of conventional detection methods.

Figure 9:
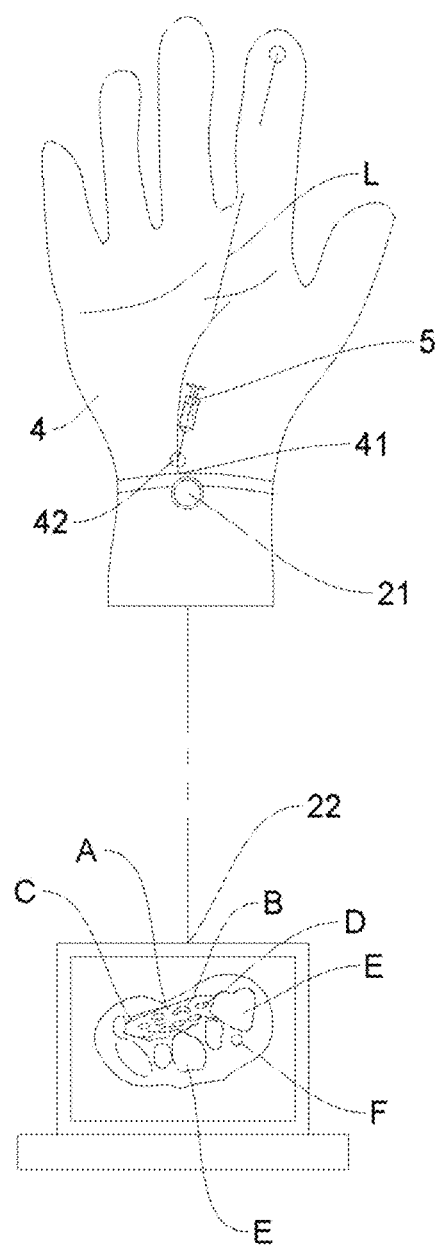
FIG. 9 is a schematic diagram of simulated injection using the detection method of the present invention.

As shown in FIG. 9, students or nursing staff can also perform simulated injection exercises through the aforementioned technique. In this embodiment, the aforementioned palm can be a simulated hand 4 made of rubber, and in the simulated hand 4 there is a soft body of carpal tunnel A and a plurality of sensors serving as nerve B, wrist ligament C, tendon D, carpal bone E, and artery F. When simulating injection, students or nursing staff also follow the steps of the present invention. The simulated hand 4 is placed on a flat surface, and a mark 42 is set 0.5 cm above the crease 41 of the simulated hand, and then the probe 21 is set to the short axis position of the simulated hand 4, and the probe unit 21 is kept parallel to the short axis, then slightly rotate the probe unit 21 to make it on the same axis L as the index finger of the simulated hand, and cooperate with the ultrasonic detection device 2 to display the position of the carpal tunnel A, and then use a simulated needle 5 for injection practice. If the carpal tunnel A is inserted correctly, a correct prompt will be generated. If the sensors such as the simulated nerve B, wrist ligament C, tendon D, carpal bone E, artery F, etc. are mistakenly touched, a wrong prompt will be generated. Students, medical staff, or resident physicians will be familiar with injections in the future and have confidence in needle insertion, which greatly reduces injection time, improves efficiency and reduces patient discomfort caused by needle insertion.

To summarize, it is clear that the composition or structure of the present invention has never been published in books or journals or used in public, therefore, it can meet the requirements for patent application, hopefully, this application can be granted favorably.

What needs to be stated is that the above statement is only specific embodiment and applied technical principle of the present invention, for any change made based on the idea of the present invention, if its function generated does not exceed the spirit covered by the present specification and its related drawings, it should all fall within the scope of what is claimed.

DESCRIPTION OF SYMBOLS

1: Palm
11: Crease
12: Mark
2: Ultrasonic detection device
21: Probe
22: Display
3: Syringe
4: Simulated hand
41: Crease
42: Mark
5: Simulated needle
A: tunnel
B: nerve
C: wrist ligament
D: tendon
E: carpal bone
F: artery

What is claimed is:

1. A method for detecting carpal tunnel using an ultrasonic detection device, consisting of:
   Step 1: laying a right-hand palm on a flat surface, with the right-hand palm facing up, and naturally straighten and open fingers to form a "5" shape;
   Step 2: setting a mark 0.5 cm above a great mound of an acupuncture point in traditional Chinese medicine, which is at a bottom of a lifeline of the right-hand palm;
   Step 3: matching with a probe of the ultrasonic detection device arranged on a short axis (0-180 degree axial direction) of a wrist joint of a test subject, and then the probe being slightly rotated near a thumb side, so that the probe is rotated along an axial direction of the mark toward a direction of an index finger;
   wherein an angle between the probe and the short axis is about 70 degrees;
   Step 4: cooperating with the ultrasonic detection device, and an image of a carpal tunnel section of the right-hand palm being obtained by the probe on a display of the ultrasonic detection device.

2. A method for detecting carpal tunnel using an ultrasonic detection device, consisting of:
   Step 1: laying a left-hand palm on a flat surface, with the left-hand palm facing up, and naturally straighten and open fingers to form a "5" shape;
   Step 2: setting a mark 0.5 cm above a great mound of an acupuncture point in traditional Chinese medicine, which is at a bottom of a lifeline of the left-hand palm;
   Step 3: matching with a probe of the ultrasonic detection device arranged on a short axis (0-180 degree axial direction) of a wrist joint of a test subject, and then the probe being slightly rotated near a thumb side, so that the probe is rotated along an axial direction of the mark toward a direction of an index finger;
   wherein, an angle between the probe and the short axis about 110 degrees;
   Step 4: cooperating with the ultrasonic detection device, and an image of a carpal tunnel section of the left-hand palm being obtained by the probe on a display of the ultrasonic detection device.

* * * * *